United States Patent
Andersch et al.

(10) Patent No.: US 7,097,848 B2
(45) Date of Patent: Aug. 29, 2006

(54) SYNERGISTIC INSECTICIDAL MIXTURES

(75) Inventors: Wolfram Andersch, Bergisch Gladbach (DE); Christoph Erdelen, deceased, late of Leichlingen (DE); by Angelika Lubos-Erdelen, legal representative, Leichlingen (DE); Peter Jeschke, Bergisch Gladbach (DE)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 10/502,527

(22) PCT Filed: Jan. 20, 2003

(86) PCT No.: PCT/EP03/00478

§ 371 (c)(1),
(2), (4) Date: Nov. 17, 2004

(87) PCT Pub. No.: WO03/063592

PCT Pub. Date: Aug. 7, 2003

(65) Prior Publication Data

US 2005/0222051 A1    Oct. 6, 2005

(30) Foreign Application Priority Data

Jan. 31, 2002   (DE) ............................... 102 03 688

(51) Int. Cl.
*A01N 43/00*   (2006.01)
*A01N 43/78*   (2006.01)
*A61K 31/425*  (2006.01)

(52) U.S. Cl. ........................ 424/405; 514/365; 514/321
(58) Field of Classification Search ................ 424/405; 514/365, 321
See application file for complete search history.

(56) References Cited

U.S. PATENT DOCUMENTS

| | | | |
|---|---|---|---|
| 3,313,684 A | 4/1967 | Schegk et al. ................ 167/30 |
| 4,310,519 A | 1/1982 | Albers-Schonberg et al. ......... 424/181 |
| 4,427,663 A | 1/1984 | Mrozik ........................ 424/180 |
| 4,510,098 A | 4/1985 | Crosby ................... 260/465 D |
| 4,510,160 A | 4/1985 | Robson ....................... 514/521 |
| 4,782,174 A | 11/1988 | Fuchs et al. ................. 558/354 |
| 4,874,749 A | 10/1989 | Mrozik ........................ 514/30 |
| 5,051,434 A | 9/1991 | Kozo et al. .................. 514/357 |
| 5,084,467 A | 1/1992 | Shiokawa et al. ........... 514/357 |
| 5,204,359 A | 4/1993 | Shiokawa et al. ........... 514/332 |
| 5,238,949 A | 8/1993 | Shiokawa et al. ........... 514/327 |
| 5,288,710 A | 2/1994 | Cvetovich ................... 514/30 |
| 5,489,603 A | 2/1996 | Uneme et al. ............... 514/365 |
| 5,633,375 A | 5/1997 | Uneme et al. ............... 544/336 |
| RE35,811 E | 5/1998 | Shiokawa et al. .......... 514/357 |
| 6,342,482 B1 * | 1/2002 | Snyder ........................ 514/31 |
| 6,559,136 B1 * | 5/2003 | Mauler-Machnik et al. .. 514/63 |
| 6,660,690 B1 * | 12/2003 | Asrar et al. ................. 504/100 |
| 6,686,387 B1 * | 2/2004 | Andersch et al. ............ 514/450 |
| 6,747,047 B1 * | 6/2004 | Lahm et al. ................. 514/341 |
| 6,828,275 B1 * | 12/2004 | Uhr et al. .................... 504/139 |
| 6,838,473 B1 * | 1/2005 | Asrar et al. ................. 514/365 |
| 6,927,210 B1 * | 8/2005 | Thompson et al. ........... 514/28 |

FOREIGN PATENT DOCUMENTS

| | | |
|---|---|---|
| EP | 1 149 532 | * 10/2001 |
| WO | 00/30440 | 6/2000 |

OTHER PUBLICATIONS

The Pesticide Manual, 11th Edition, British Crop Protection Council, (month unavailable) 1997, Editor: C.D.S. Tomlin, pp. 3-5, "Abamectin".
Journal of Organic Chemistry, vol. 59, (month unavailable) 1994, pp. 7704-7708, Raymond J. Cvetovich et al, Syntheses of 4"-epi-Amino-4"-deoxyavermectins $B_1$.
The Pesticide Manual, 11th Edition, British Crop Protection Council, (month unavailable) 1997, Editor: C.D.S. Tomlin, pp. 813-815, "Methiocarb".
The Pesticide Manual, 11th Edition, British Crop Protection Council, (month unavailable) 1997, Editor: C.D.S. Tomlin, pp. 295-296, "Beta-Cyfluthrim".
The Pesticide Manual, 11th Edition, British Crop Protection Council, (month unavailable) 1997, Editor: C.D.S. Tomlin, pp. 300-302, Lambda-Cyhalothrin.
Chem. Ind., 37, (month unavailable) 1985, pp. 730-732, Harry R. Ungerer, "Schiffsfarben—eine Spezialität der seenahen Lackindustrie".
Agricultural and Food Chemistry, vol. 9, No. 1, Jan.-Feb. 1961, pp. 30-39, C.P. Carpenter et al, "Mammalian Toxicity of 1-Naphthyl-N-methylcarbamate (Servin Insecticide)".

\* cited by examiner

*Primary Examiner*—Sabiha Qazi
(74) *Attorney, Agent, or Firm*—Richard E.L. Henderson

(57) ABSTRACT

The invention relates to insecticidal mixtures comprising the compound of the formula (I)

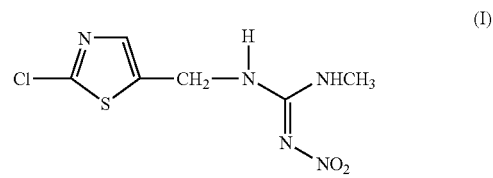

and at least one further known active compound selected from the group consisting of abamectin, emamectin or emamectin benzoate, methiocarb, β-cyfluthrin and lambda-cyhalothrin, and to the use of these mixtures for protecting plants against attack by pests.

6 Claims, No Drawings

SYNERGISTIC INSECTICIDAL MIXTURES

The present patent application has been filed under 35 U.S.C. 371 as a national stage application of PCT/EP03/00478, filed Jan. 20, 2003, which was published in German as International Patent Publication WO 03/063512 on Aug. 7, 2003, which is entitled to the right of priority of German Patent Application 102 03 688.8, filed Jan. 31, 2002.

The present invention relates to novel combinations of active compounds comprising, firstly, the known active compound clothianidin and, secondly, at least one further known insecticidally active compound, which combinations have very good insecticidal and acaricidal properties.

It is already known that clothianidin of the formula

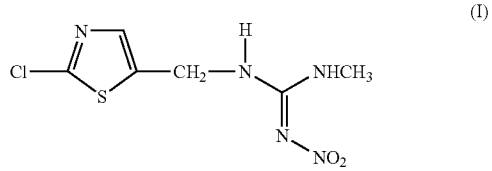

can be used for controlling animal pests, in particular insects (cf. EP-A-376 279 and EP 375 907). The activity of this compound is good; however, at low application rates or against individual pests, it is sometimes unsatisfactory.

It is also known that the compounds abamectin (II) (DE 2 717 040), emamectin (III) or emamectin benzoate (IIIa) (EP 089 202), methiocarb (IV) (U.S. Pat. No. 3,313,684), β-cyfluthrin (V) (EP 206 149) and lambda-cyhalothrin (VI) (EP 106 469) can be used for controlling insects and/or acarids.

It has now been found that mixtures, comprising clothianidin of the formula (I)

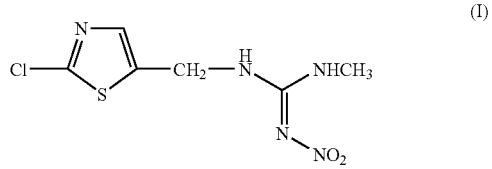

and at least one of the compounds (II), (III), (IIIa), (IV), (V) and (VI) are synergistically active and suitable for controlling animal pests. Owing to this synergism, it is possible to use considerably smaller amounts of active compounds, i.e. the activity of the mixture is greater than the activity of the individual components.

The ratio of the compound of the formula (I) used to the compounds of the formulae (II) to (VI), and the total amount of the mixture to be used depends on the nature and the occurrence of the insects and/or acarids. For each application, it is possible to determine the optimum ratios and total amounts to be used in each case by test series.

A preferred mixture according to the invention comprises the active compound clothianidin of the formula (I) and abamectin (II). Abamectin is also known from "The Pesticide Manual", 11$^{th}$ Edition, British Crop Protection Council, 1997, page 3.

In this mixture, the ratio of the active compounds can be varied within a relatively wide range. The weight ratio of clothianidin to abamectin is preferably from 1:1 to 50:1, in particular from 5:1 to 25:1.

A further preferred mixture according to the invention comprises the active compound clothianidin of the formula (I) and emamectin (III) or emamectin benzoate (IIIa). Emamectin and emamectin salts are also known as MK-244 from the Journal of Organic Chemistry, Vol. 59 (1994), 7704–7708, U.S. Pat. No. 4,874,794, U.S. Pat. No. 5,288,710 and EP-00 089 202.

In this mixture, the ratio of the active compounds can be varied within a relatively wide range. The weight ratio of clothianidin to emamectin or emamectin benzoate is preferably from 1:1 to 500:1, in particular from 100:1 to 500:1.

A further preferred mixture according to the invention comprises the active compound clothianidin of the formula (I) and methiocarb (IV). Methiocarb (IV) is also known from "The Pesticide Manual", 11$^{th}$ Edition, British Crop Protection Council, 1997, page 813.

In this mixture, the ratio of the active compounds can be varied within a relatively wide range. The weight ratio of clothianidin to methiocarb is preferably from 1:1 to 1:10, in particular from 1:1 to 1:5.

A further preferred mixture according to the invention comprises the active compound clothianidin of the formula (I) and β-cyfluthrin (V). β-cyfluthrin is also known from "The Pesticide Manual", 11$^{th}$ Edition, British Crop Protection Council, 1997, page 295.

In this mixture, the ratio of the active compounds can be varied within a relatively wide range. The weight ratio of clothianidin to β-cyfluthrin is preferably from 1:1 and 10:1, in particular from 1:1 to 6:1.

A further preferred mixture according to the invention comprises the active compound clothianidin of the formula (I) and lambda-cyhalothrin (VI). Lambda-cyhalothrin (VI) is also known from "The Pesticide Manual", 11$^{th}$ Edition, British Crop Protection Council, 1997, page 300.

In this mixture, the ratio of the active compounds can be varied within a relatively wide range. The weight ratio of clothianidin to lambda-cyhalothrin is preferably from 1:1 to 10:1, in particular from 1:1 to 6:1.

The active compound combinations are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as crop protection agents. They are active against normally sensitive and resistant species and against all or some stages of development. The abovementioned pests include:

From the order of the Isopoda, for example, *Oniscus asellus, Armadillidium vulgare* and *Porcellio scaber.*

From the order of the Diplopoda, for example, *Blaniulus guttulatus.*

From the order of the Chilopoda, for example, *Geophilus carpophagus* and *Scutigera* spp.

From the order of the Symphyla, for example, *Scutigerella immaculata.*

From the order of the Thysanura, for example, *Lepisma saccharina.*

From the order of the Collembola, for example, *Onychiurus armatus.*

From the order of the Orthoptera, for example, *Acheta domesticus, Gryllotalpa* spp., *Locusta migratoria migratorioides, Melanoplus* spp. and *Schistocerca gregaria.*

From the order of the Blattaria, for example, *Blatta orientalis, Periplaneta americana, Leucophaea maderae, Blattella germanica.*

From the order of the Dermaptera, for example, *Forficula auricularia.*

From the order of the Isoptera, for example, *Reticulitermes* spp.

From the order of the Phthiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella occidentalis.*

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae.*

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon solstitialis, Costelytra zealandica* and *Lissorhoptrus oryzophilus.*

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the class of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders, rights. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compound combinations is carried out directly or by action on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compound combinations can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

Suitable solid carriers are:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; suitable solid carriers for granules are: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; suitable emulsifiers and/or foam-formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; suitable dispersants are: for example lignosulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Possible other additives are mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H-1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl {2-methyl-1-[[[1-(4-methylphenyl)-ethyl]-amino]-carbonyl]-propyl}-carbamate, 1-(2,4-dichlorophenyl)-2-(1H-1,2,4-triazol-1-yl)-ethanone O-(phenylmethyl)oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methylbenzene, 1-[[2-(2,4-dichlorophenyl)-1,3-dioxolan-2-yl]-methyl]-1H-imidazole, 1-[[2-(4-chlorophenyl)-3-phenyloxiranyl]-methyl]-1H-1,2, 4-triazole, 1-[1-[2-[(2,4-dichlorophenyl)-methoxy]-phenyl]-ethenyl]-1H-imidazole, 1-methyl-5-nonyl-2-(phenylmethyl)-3-pyrrolidinole,
2',6'-dibromo-2-methyl-4'-trifluoromethoxy-4'-trifluoromethyl-1,3-thiazole-5-carboxanilide,
2,2-dichloro-N-[1-(4-chlorophenyl)ethyl]-1-ethyl-3-methyl-cyclopropanecarboxamide,
2,6-dichloro-5-(methylthio)-4-pyrimidinyl-thiocyanate,
2,6-dichloro-N-(4-trifluoromethylbenzyl)benzamide,
2,6-dichloro-N-[[4-(trifluoromethyl)phenyl]methyl]benzamide,
2-(2,3,3-triiodo-2-propenyl)-2H-tetrazole,
2-[(1-methylethyl)sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo[2,3-d]pyrimidine-5-carbonitrile,
2-aminobutane,
2-bromo-2-(bromomethyl)pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)acetamide,
2-phenylphenol (OPP),
3,4-dichloro-1-[4-(difluoromethoxy)phenyl]-1H-pyrrole-2,5-dione,
3,5-dichloro-N-[cyano[(1-methyl-2-propynyl)oxy]methyl]benzamide,
3-(1,1-dimethylpropyl-1-oxo)-1H-indene-2-carbonitrile,
3-[2-(4-chlorophenyl)-5-ethoxy-3-isoxazolidinyl]pyridine,
4-chloro-2-cyano-N,N-dimethyl-5-(4-methylphenyl)-1H-imidazole-1-sulphonamide,
4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)carbonyl]-9-carboxylic hydrazide,
bis(1-methylethyl)-3-methyl-4-[(3-methylbenzoyl)oxy]-2,5-thiophenedicarboxylate,
cis-1-(4-chlorophenyl)-2-(1H-1,2,4-triazol-1-yl)cycloheptanol,
cis-4-[3-[4-(1,1-dimethylpropyl)phenyl-2-methylpropyl]-2,6-dimethylmorpholine hydrochloride,
ethyl [(4-chlorophenyl)azo]cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)acetamide,
N-(2,6-dimethylphenyl)-2-methoxy-N-(tetrahydro-2-oxo-3-thienyl)acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)acetamide,
N-(6-methoxy)-3-pyridinyl)cyclopropanecarboxamide,
N-[2,2,2-trichloro-1-[(chloroacetyl)amino]ethyl]benzamide,
N-[3-chloro-4,5-bis(2-propinyloxy)phenyl]-N'-methoxymethanimidamide,
N-formyl-N-hydroxy-DL-alanine-sodium salt,
O,O-diethyl[2-(dipropylamino)-2-oxoethyl]ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one, Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alpha-cypermethrin, alphamethrin, amitraz, avermectin, AZ 60541, azadirachtin, azamethiphos, azinphos A, azinphos M, azocyclotin,
*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben,
cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrip, clocythrin, cloethocarb, clofentezine, cyanophos, cycloprene, cycloprothrin, cyfluthrin, cyhalothrin, cyhexatin, cypernethrin, cyromazine,
deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn,
eflusilanate, emamectin, empenthrin, endosulfan, *Entomopfthora* spp., esfenvalerate, ethiofencarb, ethion, ethoprophos, etofenprox, etoxazole, etrimfos,
fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb,
granulosis viruses,
halofenozide, HCH, heptenophos, hexaflumuron, hexythiazox, hydroprene,
imidacloprid, indoxacarb, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propargite, propoxur, prothiofos, prothoate, pymetrozine, pyraclofos, pyresmethrin, pyrethrum, pyridaben, pyridathion, pyrimidifen, pyriproxyfen, quinalphos,
ribavirin,
salithion, sebufos, silafluofen, spinosad, spirodiclofen, spiromesifen, sulfotep, sulprofos,
tau-fluvalinate, tebufenozide, tebufenpyrad, tebupirimiphos, teflubenzuron, tefluthrin, temephos, temivinphos, terbufos, tetrachlorvinphos, theta-cypermethrin, thiacloprid thiamethoxam, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb,
vamidothion, vaniliprole, *Verticillium lecanii*,
YI 5302,
zeta-cypermethrin, zolaprofos,
(1R-cis)-[5-(phenylmethyl)-3-furanyl]methyl 3-[(dihydro-2-oxo-3(2H)furanylidene)-methyl]-2,2-dimethylcyclopropanecarboxylate,
(3-phenoxyphenyl)methyl 2,2,3,3-tetramethylcyclopropanecarboxylate,
1-[(2-chloro-5-thiazolyl)methyl]tetrahydro-3,5-dimethyl-N-nitro-1,3,5-triazine-2(1H)-imine,
2-(2-chloro-6-fluorophenyl)-4-[4-(1,1-dimethylethyl)phenyl]-4,5-dihydrooxazole,
2-(acetyloxy)-3-dodecyl-1,4-naphthalenedione,
2-chloro-N-[[[4-(1-phenylethoxy)phenyl]amino]carbonyl]benzamide,
2-chloro-N-[[[4-(2,2-dichloro-1,1-difluoroethoxy)phenyl]amino]carbonyl]-benzamide,
3-methylphenyl propylcarbamate,
4-[4-(4-ethoxyphenyl)-4-methylpentyl]-1-fluoro-2-phenoxybenzene,
4-chloro-2-(1,1-dimethylethyl)-5-[[2-(2,6-dimethyl-4-phenoxyphenoxy)ethyl]thio]-3(2H)-pyridazinone,
4-chloro-2-(2-chloro-2-methylpropyl)-5-[(6-iodo-3-pyridinyl)methoxy]-3(2H)-pyrida
4-chloro-5-[(6-chloro-3-pyridinyl)methoxy]-2-(3,4-dichlorophenyl)-3(2H)-pyridazinone,

*Bacillus thuringiensis* strain EG-2348,
[2-benzoyl-1-(1,1-dimethylethyl)hydrazinobenzoic acid,
2,2-dimethyl-3-(2,4-dichlorophenyl)-2-oxo-1-oxaspiro[4.5]dec-3-en-4-yl butanoate,
[3-[(6-chloro-3-pyridinyl)methyl]-2-thiazolidinylidene]cyanamide,
dihydro-2-(nitromethylene)-2H-1,3-thiazine-3(4H)carboxaldehyde,
ethyl[2-[[1,6-dihydro-6-oxo-1-(phenylmethyl)-4-pyridazinyl]oxy]ethyl]carbamate,
N-(3,4,4-trifluoro-1-oxo-3-butenyl)glycine,
N-(4-chlorophenyl)-3-[4-(difluoromethoxy)phenyl]-4,5-dihydro-4-phenyl-1H-pyrazole-1-carboxamide,
N-methyl-N'-(1-methyl-2-propenyl)-1,2-hydrazinedicarbothioamide,
N-methyl-N'-2-propenyl-1,2-hydrazinedicarbothioamide,
O,O-diethyl[2-(dipropylamino)-2-oxoethyl]-ethylphosphoramidothioate.

It is also possible to admix other known active compounds, such as herbicides or fertilizers and growth regulators.

When used as insecticides, the active compound combinations according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound combinations are distinguished by an excellent residual action on wood and clay as well as a good stability to alkali on limed substrates.

The active compound combinations according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acaria (Acarida) and the orders of the Meta- and Mesostigmata, for example, *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) und Acaridida (Astigmata), for example, *Acarapis* spp., *Cheyletiella* spp., *Omithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compound combinations according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey, etc.) should be diminished, so that more economic and easier animal husbandry is possible by use of the active compounds according to the invention.

The active compound combinations according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the active compound combinations according to the invention also have a strong insecticidal action against insects which destroy industrial materials.

The following insects may be mentioned as examples and as preferred—but without limitation:

Beetles, such as

*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as

*Sirex juvencus, Urocerus gigas, Urocerus gigas taignus, Urocerus augur.*

Termites, such as

*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning non-living materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example:

building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compound combinations can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic-chemical solvent or solvent mixture and/or an oily or oil-like organic-chemical solvent or solvent mixture of low volatility and/or a polar organic-chemical solvent or solvent mixture and/or water, and if appropriate an emulsifier and/or wetting agent.

Organic-chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic-chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic-chemical solvent or solvent mixture is replaced by an aliphatic polar organic-chemical solvent or solvent mixture. Aliphatic organic-chemical solvents containing hydroxyl and/or ester and/or ether groups, such as, for example, glycol ethers, esters or the like, are preferably used.

Organic-chemical binders which are used in the context of the present invention are the synthetic resins and/or binding drying oils which are known per se, are water-dilutable and/or are soluble or dispersible or emulsifiable in the organic-chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic-chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic-chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

The active compound combinations according to the invention can also be used for protecting against colonization of articles, especially ships hulls, screens, nets, constructions, quays and signalling equipment, which come into contact with seawater or brackish water.

Colonization by sessile Oligochaetae, such as *Serpulidae*, and by shellfish and species of the group *Ledamorpha* (goose barnacles), such as various *Lepas* and *Scalpellum* species, or by species of the group *Balanomorpha* (acorn barnacles), such as *Balanus* or *Pollicipes* species, increases the frictional resistance of ships and leads as a result, through increased energy consumption and frequent spells in dry dock, to a marked increase in the operating costs.

In addition to colonization by algae, for example *Ectocarpus* sp. and *Ceramium* sp., particular importance is attached to infestation by sessile *Entomostraca* groups, which are comprised under the name *Cirripedia* (cirriped crustacea).

Surprisingly, it has now been found that the active compound combinations according to the invention have a good antifouling (anti-colonization) effect.

By using active compound combinations according to the invention it is possible to dispense with the use of heavy metals, such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)tin, tributyltin oxide, molybdenum disulphide, antimony oxide, polymeric butyl titanate, phenyl(bispyridine)bismuth chloride, tri-n-butyltin fluoride, manganese ethylenebisthiocarbamate, zinc dimethyl-dithiocarbamate, zinc ethylenebisthiocarbamate, the zinc and copper salts of 2-pyridinethiol 1-oxide, bisdimethyldithiocarbamoylzinc ethylenebisthiocarbamate, zinc oxide, copper(I) ethylenebisdithiocarbamate, copper thiocyanate, copper naphthenate and tributyltin halides, or substantially to reduce the concentration of these compounds.

If appropriate, the ready-to-use antifouling paints may comprise yet further active compounds, preferably algicides, fungicides, herbicides, molluscicides or other active antifouling active compounds.

Preferred co-components for the antifouling compositions according to the invention are:

algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
cyclohexylbenzo[b]thiophenecarboxamide S,S-dioxide, dichlofluanid, fluorfolpet, 3-iodo-2-propinyl butylcarbamate, tolylfluanid and azoles such as azaconazole, cyproconazole, epoxyconazole, hexaconazole, metconazole, propiconazole and tebuconazole;

molluscicides such as
Fe-chelating agents fentin acetate, metaldehyde, methiocarb, niclosamid, thiodicarb and trimethacarb;

or customary active antifouling compounds such as
4,5-dichloro-2-octyl-4-isothiazolin-3-one, diiodomethyl paratryl sulfone, 2-(N,N-dimethylthiocarbamoylthio)-5-nitrothiazyl, potassium, copper, sodium and zinc salts of 2-pyridinethiole 1-oxide, pyridine triphenylborane, tetrabutyldistannoxane, 2,3,5,6-tetrachloro-4-(methylsulphonyl)-pyridine, 2,4,5,6-tetrachloroisophthalonitrile, tetramethylthiuram disulphide and 2,4,6-trichlorophenylmaleimide.

The antifouling compositions used comprise the active compound in a concentration of from 0.001 to 50% by weight, in particular from 0.01 to 20% by weight.

The antifouling compositions furthermore comprise the customary components as described, for example, in Ungerer, *Chem. Ind.* 1985, 37, 730–732 and Williams, Antifouling Marine Coatings, Noyes, Park Ridge, 1973.

In addition to the algicidal, fungicidal, molluscicidal and insecticidal active compounds, antifouling coating compositions comprise, in particular, binders.

Examples of acknowledged binders are polyvinyl chloride in a solvent system, chlorinated rubber in a solvent system, acrylic resins in a solvent system especially in an aqueous system, vinyl chloride/vinyl acetate copolymer systems in the form of aqueous dispersions or in the form of organic solvent systems, butadiene/styrene/acrylonitrile rubbers, drying oils, such as linseed oil, resin esters or modified hard resins in combination with tar or bitumen, asphalt and also epoxy compounds, small amounts of chlorinated rubber, chlorinated polypropylene and vinyl resins.

The coating compositions also optionally include inorganic pigments, organic pigments or dyestuffs, which are preferably insoluble in salt water. The coating compositions may also comprise materials such as rosin, for a controlled release of the active compounds. The coats may also include plasticizers, modifying agents which influence the rheological properties, and other conventional constituents. The active compound combinations according to the invention can also be incorporated into self-polishing antifouling systems.

The active compounds are also suitable for controlling animal pests, in particular insects, arachnids and mites, which are encountered in closed rooms, such as, for example, flats, factory halls, offices, vehicle cabins and the like. They can be used on their own or in combination with other active compounds and auxiliaries in household insecticidal products for controlling these pests. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of the household insecticides, they are used on their own or in combination with other suitable active compounds, such as phosphoric acid esters, carbamates, pyrethroids, growth regulators or active compounds from other known classes of insecticides.

Application is carried out in the form of aerosols, unpressurized sprays, for example pump and atomizer sprays, nebulizers, foggers, foams, gels, vaporizer products with vaporizer tablets made of cellulose or plastic, liquid vaporizers, gel and membrane vaporizers, propeller-operated vaporizers, energyless or passive vaporizer systems, moth papers, moth sachets and moth gels, as granules or dusts, in baits for scattering or bait stations.

When using the active compound combinations according to the invention, the application rates can be varied within a relatively wide range, depending on the kind of application. In the treatment of parts of plants, the application rates of the active compound combination are generally between 0.1 and 10 000 g/ha, preferably between 10 and 1 000 g/ha.

The good insecticidal and acaricidal activity of the active compound combinations according to the invention is evident from the examples below. While the individual active compounds exhibit weaknesses with regard to activity, the combinations have an activity which exceeds a simple addition of activities.

A synergistic effect of insecticides and acaricides is always present when the activity of the active compound combinations exceeds the total of the activities of the active compounds when applied individually.

Formula for the Calculation of the Synergistic Activity of a Combination of Two Active Compounds The expected activity for a given combination of two active compounds can be calculated as follows (cf. Carpenter, C. S., "Mammalian Toxicity of 1-naphthyl-N-methyl-carbamate [Sevin Insecticide]", Agricultural and Food Chemistry, Vol. 9, No. 1, pages 30–39, 1961):

If

Pa is the proportion of active compound A in the mixture,

Pb is the proportion of active compound B in the mixture, $LC_{50\ (or\ 95)}a$ is the concentration at which 50% (or 95%) of the animals treated with active compound A are killed and $LC_{50\ (or\ 95)}b$ is the concentration at which 50% (or 95%) of the animals treated with active compound B are killed, $$\text{the expected } LC_{50 (or\ 95)} (comb.) = \frac{1}{\dfrac{Pa}{LC_{50(or\ 95)}a} + \dfrac{Pb}{LC_{50(or\ 95)}b}}$$

If the calculated $LC_{50\ (or\ 95)}$ exceeds the value actually obtained and is higher than the confidence interval, the activity of the combination is superadditive, i.e. a synergistic effect exists.

USE EXAMPLES

Example A

*Heliothis armigera* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soya bean shoots (*glycine max*) are treated by being dipped into the preparation of active compound of the desired concentration and are populated with *Heliothis armigera* caterpillars while the leaves are still moist.

After the desired period of time, the kill in % is determined. 100% means that all caterpillars have been killed; 0% means that none of the caterpillars have been killed. The determined kill rates are inserted into Carpenter's formula (see preceding page).

In this test, the following combination of active compounds in accordance with the present application showed a synergistically enhanced activity compared to the active compounds applied individually:

TABLE A

| Plant-damaging insects *Heliothis armigera* test | |
|---|---|
| Active compounds | $LC_{50}$ after 6 days |
| β-cyfluthrin | 0.159 ppm |
| clothianidin | 0.997 ppm |
| β-cyfluthrin + clothianidin (1:6) according to the invention | calc.**0.569 ppm found*0.1 ppm | found*= activity found
calc.**= activity calculated using Carpenter's formula

Example B

Myzus Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*), which are heavily infested by the green peach aphid (*Myzus persicae*) are treated by being dipped into the preparation of active compound of the desired concentration.

After the desired period of time, the killed in % is determined. 100% means that all aphids have been killed. The determined kill rates are inserted into Carpenter's formula.

In this test, the following combination of active compounds in accordance with the present application showed a synergistically enhanced activity compared to the active compounds applied individually:

TABLE B

| Plant-damaging insects *Myzus* test | |
|---|---|
| Active compounds | $LC_{50}$ after 6 days |
| β-cyfluthrin | 2.583 ppm |
| clothianidin | 1.013 ppm |
| β-cyfluthrin + clothianidin (1:1.2) according to the invention | calc.**1.399 ppm found*0.224 ppm | found*= activity found
calc.**= activity calculated using Carpenter's formula

Example C

*Plutella* Test, Sensitive Strain

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moths (*Plutella xylostella*, sensitive strain) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE C

| plant-damaging insects *Plutella* test, sensitive strain | |
|---|---|
| Active compounds | $LC_{95}$ after 6 days |
| β-cyfluthrin | 0.699 ppm |
| clothianidin | 42.493 ppm |

TABLE C-continued plant-damaging insects
*Plutella* test, sensitive strain

| Active compounds | LC$_{95}$ after 6 days |
|---|---|
| β-cyfluthrin + clothianidin (1:6) according to the invention | calc.**4.444 ppm found*0.19 ppm | found*= activity found
calc.**= activity calculated using Carpenters formula

Example D

*Phaedon* Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are inserted in Carpenter's formula.

In this test, the following combination of active compounds in accordance with the present application showed a synergistically enhanced activity compared to the active compounds applied individually:

TABLE D

Plant-damaging insects
*Phaedon* larvae test

| Active compounds | LC$_{50}$ after 6 days |
|---|---|
| β-cyfluthrin | 0.646 ppm |
| clothianidin | 6.708 ppm |
| β-cyfluthrin + clothianidin (1:6) according to the invention | calc.**2.865 ppm found*0.389 ppm | found*= activity found
calc.**= activity calculated using Carpenter's formula

Example E

*Spodoptera frugiperda* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE E

Plant-damaging insects
*Spodoptera frugiperda* test

| Active compounds | LC$_{95}$ after 3 days |
|---|---|
| β-cyfluthrin | 1.113 ppm |
| clothianidin | 6.099 ppm |
| β-cyfluthrin + clothianidin (1:6) according to the invention | calc.**3.717 ppm found*0.5 ppm | found*= activity found
calc.**= activity calculated using Carpenter's formula

Example F

*Heliothis armigera* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soya bean shoots (*glycine max*) are treated by being dipped into the preparation of active compound of the desired concentration and are populated with *Heliothis armigera* caterpillars while the leaves are still moist.

After the desired period of time, the kill in % is determined. 100% means that all caterpillars have been killed; 0% means that none of the caterpillars have been killed. The determined kill rates are inserted into Carpenter's formula.

In this test, the following combination of active compounds in accordance with the present application showed a synergistically enhanced activity compared to the active compounds applied individually:

TABLE F

Plant-damaging insects
*Heliothis armigera* test

| Active compounds | LC$_{50}$ after 6 days |
|---|---|
| avermectin | 0.094 ppm |
| clothianidin | 15.0 ppm |

TABLE F-continued

| | Plant-damaging insects<br>Heliothis armigera test |
|---|---|
| Active compounds | LC$_{50}$ after 6 days |
| avermectin + clothianidin (1:25)<br>according to the invention | calc.**2.137 ppm<br>found*0.094 ppm | found*= activity found
calc.**= activity calculated using Carpenter's formula

Example G

*Phaedon* Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are inserted in Carpenter's formula.

In this test, the following combination of active compounds in accordance with the present application showed a synergistically enhanced activity compared to the active compounds applied individually:

TABLE G

| | Plant-damaging insects<br>*Phaedon* larvae test |
|---|---|
| Active compounds | LC$_{95}$ after 6 days |
| avermectin | 1.431 ppm |
| clothianidin | 11.234 ppm |
| avermectin + clothianidin (1:25)<br>according to the invention | calc.**8.850 ppm<br>found*0.449 ppm | found*= activity found
calc.**= activity calculated using Carpenter's formula

Example H

*Myzus* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*), which are heavily infested by the green peach aphid (*Myzus persicae*) are treated by being dipped into the preparation of active compound of the desired concentration.

After the desired period of time, the killed in % is determined. 100% means that all aphids have been killed; 0% means that none of the aphids have been killed. The determined kill rates are inserted into Carpenter's formula.

In this test, the following combination of active compounds in accordance with the present application showed a synergistically enhanced activity compared to the active compounds applied individually:

TABLE H

| | Plant-damaging insects<br>*Myzus* test |
|---|---|
| Active compounds | LC$_{95}$ after 1 day |
| methiocarb | 75.000 ppm |
| clothianidin | 5.988 ppm |
| methiocarb + clothianidin (5:1)<br>according to the invention | calc.**25.641 ppm<br>found*1.255 ppm | found*= activity found
calc.**= activity calculated using Carpenter's formula

Example I

*Spodoptera frugiperda* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE I

| | Plant-damaging insects<br>*Spodoptera frugiperda* test |
|---|---|
| Active compounds | LC$_{50}$ after 6 days |
| methiocarb | 51.649 ppm |
| clothianidin | 2.450 ppm |

TABLE I-continued

Plant-damaging insects
*Spodoptera frugiperda* test

| Active compounds | LC$_{50}$ after 6 days |
| --- | --- |
| methiocarb + clothianidin (1:1) according to the invention | calc.**4.673 ppm found*0.993 ppm | found*= activity found
calc.**= activity calculated using Carpenter's formula

Example J

*Heliothis armigera* Test

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Soya bean shoots (*glycine max*) are treated by being dipped into the preparation of active compound of the desired concentration and are populated with *Heliothis armigera* caterpillars while the leaves are still moist.

After the desired period of time, the kill in % is determined. 100% means that all caterpillars have been killed; 0% means that none of the caterpillars have been killed. The determined kill rates are inserted into Carpenter's formula.

In this test, the following combination of active compounds in accordance with the present application showed a synergistically enhanced activity compared to the active compounds applied individually:

TABLE J

Plant-damaging insects
*Heliothis armigera* test

| Active compounds | LC$_{50}$ after 6 days |
| --- | --- |
| emamectin benzoate | 0.007 ppm |
| clothianidin | 3.527 ppm |
| emamectin benzoate + clothianidin (1:500) according to the invention | calc.**1.757 ppm found*0.004 ppm | found*= activity found
calc.**= activity calculated using Carpenter's formula

Example K

*Phaedon* Larvae Test

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are inserted in Carpenter's formula.

In this test, the following combination of active compounds in accordance with the present application showed a synergistically enhanced activity compared to the active compounds applied individually:

TABLE K

Plant-damaging insects
*Phaedon* larvae test

| Active compounds | LC$_{95}$ after 6 days |
| --- | --- |
| emamectin benzoate | 0.072 ppm |
| clothianidin | 17.504 ppm |
| emamectin benzoate + clothianidin (1:100) according to the invention | calc.**5.102 ppm found*0.082 ppm | found* = activity found
calc.** = activity calculated using Carpenter's formula

Example L

*Plutella* Test, Sensitive Strain

| Solvent: | 7 parts by weight of dimethylformamide |
| --- | --- |
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moths (*Plutella xylostella*, sensitive strain) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE L

Plant-damaging insects
*Plutella* test, sensitive strain

| Active compounds | LC$_{95}$ after 6 days |
| --- | --- |
| emamectin benzoate | 0.0009 ppm |
| clothianidin | 9.045 ppm |

TABLE L-continued

Plant-damaging insects
Plutella test, sensitive strain

| Active compounds | LC$_{95}$ after 6 days |
|---|---|
| Emamectin benzoate + clothianidin (1:500) according to the invention | calc.**0.429 ppm found*0.0027 ppm | found* = activity found
calc.** = activity calculated using Carpenter's formula

Example M

*Plutella* Test, Resistant Strain

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moths (*Plutella xylostella*, resistant strain) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE M

Plant-damaging insects
Plutella test, resistant strain

| Active compounds | LC$_{50}$ after 6 days |
|---|---|
| emamectin benzoate | 0.0012 ppm |
| clothianidin | 27.271 ppm |
| emamectin benzoate + clothianidin (1:500) according to the invention | calc.**0.587 ppm found*0.0008 ppm | found* = activity found
calc.** = activity calculated using Carpenter's formula

Example N

*Spodoptera frugiperda* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the armyworm (*Spodoptera frugiperda*) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE N

Plant-damaging insects
Spodoptera frugiperda test

| Active compounds | LC$_{50}$ after 6 days |
|---|---|
| emamectin benzoate | 0.003 ppm |
| clothianidin | 0.178 ppm |
| emamectin benzoate + clothianidin (1:500) according to the invention | calc.**0.159 ppm found*0.0027 ppm | found* = activity found
calc.** = activity calculated using Carpenter's formula

Example O

*Aphis gossypii* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cotton leaves (*Gossypium hirsutum*), which are heavily infested by the cotton aphid (*Aphis gossypii*) are treated by being dipped into the preparation of active compound of the desired concentration.

After the desired period of time, the killed in % is determined. 100% means that all aphids have been killed; 0% means that none of the aphids have been killed. The determined kill rates are inserted into Carpenter's formula.

In this test, the following combination of active compounds in accordance with the present application showed a synergistically enhanced activity compared to the active compounds applied individually:

TABLE O

Plant-damaging insects
Aphis gossypii test

| Active compounds | LC$_{95}$ after 6 days |
|---|---|
| lambda-cyhalothrin | 10.545 ppm |
| clothianidin | 4.954 ppm |
| lambda-cyhalothrin + clothianidin (1:1) according to the invention | calc.**6.757 ppm found*<0.6 ppm | found* = activity found
calc.** = activity calculated using Carpenter's formula

Example P

*Myzus* Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent and emulsifier, and the concentrate is diluted with emulsifier-containing water to the desired concentration.

Cabbage leaves (*Brassica oleracea*), which are heavily infested by the green peach aphid (*Myzus persicae*) are treated by being dipped into the preparation of active compound of the desired concentration.

After the desired period of time, the killed in % is determined. 100% means that all aphids have been killed; 0% means that none of the aphids have been killed. The determined kill rates are inserted into Carpenter's formula.

In this test, the following combination of active compounds in accordance with the present application showed a synergistically enhanced activity compared to the active compounds applied individually:

TABLE P

| Plant-damaging insects *Myzus* test | |
|---|---|
| Active compounds | $LC_{95}$ after 1 day |
| lambda-cyhalothrin | 11.234 ppm |
| clothianidin | 1.303 ppm |
| lambda-cyhalothrin + clothianidin (1:1) | calc.**2.331 ppm |
| according to the invention | found*0.6 ppm | found*= activity found
calc.**= activity calculated using Carpenter's formula

Example Q

*Phaedon* Larvae Test

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent emulsifier, and the concentrate is diluted with emulsifier-containing water to the desired concentration.

Cabbage leaves (*Brassica oleracea*) are treated by being dipped into the preparation of active compound of the desired concentration and are populated with larvae of the mustard beetle (*Phaedon cochleariae*) while the leaves are still moist.

After the desired period of time, the kill in % is determined. 100% means that all beetle larvae have been killed; 0% means that none of the beetle larvae have been killed. The determined kill rates are inserted in Carpenter's formula.

In this test, the following combination of active compounds in accordance with the present application showed a synergistically enhanced activity compared to the active compounds applied individually:

TABLE Q

| Plant-damaging insects *Phaedon* larvae test | |
|---|---|
| Active compounds | $LC_{95}$ after 6 days |
| lambda-cyhalothrin | 11.234 ppm |
| clothianidin | 7.690 ppm |
| lambda-cyhalothrin + clothianidin (1:1) | calc.**9.09 ppm |
| according to the invention | found*0.6 ppm | found*= activity found
calc.**= activity calculated using Carpenter's formula

Example R

*Plutella* Test, Sensitive Strain

| Solvent: | 7 parts by weight of dimethylformamide |
|---|---|
| Emulsifier: | 2 parts by weight of alkylaryl polyglycol ether |

To produce a suitable preparation of active compound, 1 part by weight of active compound is mixed with the stated amounts of solvent emulsifier, and the concentrate is diluted with emulsifier-containing water to the desired concentration.

Cabbage leaves (*Brassica oleracea*) are treated by being dipped into the preparation of active compound of the desired concentration and are populated with caterpillars of the diamondback moths (*Plutella xylostella*, sensitive strain) while the leaves are still moist.

After the desired period of time, the kill in % is determined. 100% means that all caterpillars have been killed; 0% means that none of the caterpillars have been killed. The determined kill rates are inserted in Carpenter's formula.

In this test, the following combination of active compounds in accordance with the present application showed a synergistically enhanced activity compared to the active compounds applied individually:

TABLE R

| Plant-damaging insects *Plutella* test, sensitive strain | |
|---|---|
| Active compounds | $LC_{95}$ after 6 days |
| lambda-cyhalothrin | 0.09 ppm |
| clothianidin | 28.46 ppm |
| lambda-cyhalothrin + clothianidin (1:125) | calc.**8.065 ppm |
| according to the invention | found*0.22 ppm | found*= activity found
calc.**= activity calculated using Carpenter's formula

What is claimed is:

1. A composition for controlling animal pests comprising a synergistically active mixture of clothianidin of formula (I)

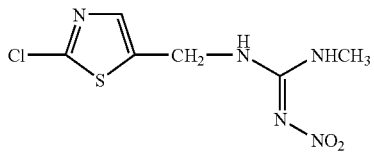

and one or more compounds selected from the group consisting of abamectin, emamectin or emamectin benzoate, and methiocarb.

2. A composition according to claim 1 for controlling animal pests comprising a synergistically active mixture of clothianidin and abamectin.

3. A composition according to claim 1 for controlling animal pests comprising a synergistically active mixture of clothianidin and emamectin or emamectin benzoate.

4. A composition according to claim 1 for controlling animal pests comprising a synergistically active mixture of clothianidin and methiocarb.

5. A method for controlling animal pests comprising applying an effective amount of a composition according to claim 1 to animal pests and/or their habitat.

6. A process for preparing pesticides comprising mixing a synergistically active mixture according to claim 1 with one or more extenders and/or surfactants.

* * * * *